(12) United States Patent
Okun et al.

(10) Patent No.: US 7,655,594 B2
(45) Date of Patent: Feb. 2, 2010

(54) MATERIALS FOR DEGRADING CONTAMINANTS

(75) Inventors: Neyla Okun, Alpharetta, GA (US); Craig L. Hill, Atlanta, GA (US)

(73) Assignee: Emory University, Atlanta, GA (US)

( * ) Notice: Subject to any disclaimer, the term of this patent is extended or adjusted under 35 U.S.C. 154(b) by 815 days.

(21) Appl. No.: 10/512,336

(22) PCT Filed: May 5, 2003

(86) PCT No.: PCT/US03/14375

§ 371 (c)(1), (2), (4) Date: Oct. 21, 2004

(87) PCT Pub. No.: WO03/094977

PCT Pub. Date: Nov. 20, 2003

(65) Prior Publication Data

US 2005/0159307 A1 Jul. 21, 2005

Related U.S. Application Data

(60) Provisional application No. 60/377,740, filed on May 3, 2002.

(51) Int. Cl.
*B01J 21/00* (2006.01)
*B01J 23/00* (2006.01)
*B01J 23/10* (2006.01)
*B01J 23/02* (2006.01)
*B01J 23/04* (2006.01)
*B01J 23/06* (2006.01)
*G21F 9/00* (2006.01)
*G21F 9/16* (2006.01)
*C04B 35/14* (2006.01)
*C04B 35/16* (2006.01)
*C07F 7/22* (2006.01)

(52) U.S. Cl. ............... 502/302; 502/240; 502/241; 502/242; 502/243; 502/246; 502/250; 502/254; 502/258; 502/304; 502/305; 502/325; 502/340; 502/344; 588/1; 588/14; 588/15; 588/901; 501/133; 556/28

(58) Field of Classification Search ......... 502/240–262, 502/302–322, 325–354, 407, 439; 501/133; 588/200, 205–207, 215, 218, 221, 238, 242, 588/244, 1, 14, 15, 901
See application file for complete search history.

(56) References Cited

U.S. PATENT DOCUMENTS

| | | | |
|---|---|---|---|
| 5,053,084 A | 10/1991 | Masumoto et al. | 148/11.5 A |
| 5,314,657 A | 5/1994 | Ostlund | 419/15 |
| 5,391,638 A | 2/1995 | Katsoulis et al. | 525/389 |
| 5,541,017 A | 7/1996 | Hong et al. | 429/59 |
| 5,548,052 A | 8/1996 | Katsoulis et al. | 528/10 |
| 5,885,922 A | 3/1999 | Hibst et al. | 502/305 |
| 6,020,369 A | 2/2000 | Schinazi et al. | 514/492 |
| 6,420,434 B1 * | 7/2002 | Braue et al. | 514/759 |
| 6,713,076 B1 * | 3/2004 | Hill et al. | 424/402 |
| 6,723,349 B1 * | 4/2004 | Hill et al. | 424/604 |
| 7,097,858 B2 * | 8/2006 | Hill et al. | 424/604 |
| 7,514,577 B2 * | 4/2009 | Kortz et al. | 556/28 |
| 2004/0185078 A1 * | 9/2004 | Hill et al. | 424/402 |

OTHER PUBLICATIONS

"Polyoxymetalates on cationic silica: Highly selective and efficient O2/air-based oxidation of 2-chloroethyl ethyl sulfide at ambient temperature," Nelya M. Okun et al. Journal of Molecular Catalysis A: Chemical 197 (2003), pp. 283-290.*

"A novel organic/inorganic hybrid nanoporous material incorporating Keggin-type polyoxometalates," Lan Yang, et al. Inorganic Chemistry Communications 6 (2003), pp. 1020-1024.*

"Immobilization of a Mo, V-polyoxometalate on cationically modified mesoporous silica: Synthesis and characterization studies," Dharmesh Kumar et al. Macroporous and Mesoporous Materials 98 (2007), pp. 309-316.*

* cited by examiner

*Primary Examiner*—Patricia L Hailey
(74) *Attorney, Agent, or Firm*—Thomas, Kayden, Horstemeyer & Risley, LLP

(57) ABSTRACT

Briefly described, compositions, materials including the compositions, methods of using the compositions, and methods of degrading contaminants, are described herein. The composition can include a polyoxometalate/ cationic silica material. In addition, the compositions can be made of a polyoxometalate/cationic silica material, a copper (II) salt having a weakly bound anion, and a nitrate salts. Further, the compositions can be made of a polyoxometalate/cationic silica material, a copper (II) salt having a weakly bound anion, a compound selected from tetraethylammonium (TEA) nitrate, tetra-n-butylammonium (TBA) nitrate, and combinations thereof.

31 Claims, No Drawings

MATERIALS FOR DEGRADING CONTAMINANTS

CROSS-REFERENCE TO RELATED APPLICATION

This application claims priority to U.S. provisional application entitled, "MATERIALS FOR DEGRADING CONTAMINANTS," having Ser. No. 60/377,740, filed May 3, 2002, which is entirely incorporated herein by reference.

STATEMENT REGARDING FEDERALLY SPONSORED RESEARCH OR DEVELOPMENT

The U.S. government may have a paid-up license in this invention and the right in limited circumstances to require the patent owner to license others on reasonable terms as provided for by the terms of DAAH01-01-C-R189 awarded by the Defense Advanced Research Project Agency (DARPA).

TECHNICAL FIELD

The present invention is generally related to materials for protection and/or decontamination of contaminants and, more particularly, is related to compositions having polyoxometalate/cationic silica materials, copper (II) salts, and/or transition metal nitrates, which can be used for protection against and/or decontamination of contaminants.

BACKGROUND

Decreasing the danger of contaminants, such as warfare agents, aldehydes, and sulfur compounds, has long been a significant issue. Materials that can protect and/or remove contaminants from the environment in which people, such as military or office personnel, are operating can significantly decrease problems associated with those contaminants. Various materials have been used, but in many instances the materials do not protect and/or remove contaminants in an efficacious manner. Thus, a heretofore unaddressed need exists in the industry to develop materials that are effective against contaminants.

SUMMARY

Briefly described, embodiments of the present invention include compositions, materials including the compositions, methods of using the compositions, and methods of degrading contaminants, each of which are described in more detail below. The composition can be made of a polyoxometalate/cationic silica material. In addition, the compositions can be made of a polyoxometalate/cationic silica material, a copper (II) salt having a weakly bound anion, and a transition metal nitrate. Further, the compositions can be made of a polyoxometalate/cationic silica material, a copper (II) salt having a weakly bound anion, and a compound selected from tetraethylammonium (TEA) nitrate, tetra-n-butylammonium (TBA) nitrate, and combinations thereof.

Another embodiment includes material for degrading a contaminant. The material can include topical carriers, coatings, powders, and fabrics, where the material includes one or more of the compositions described herein.

A representative embodiment also includes a method of degrading contaminants. The method includes providing a material described herein, contacting the material with the contaminant in the presence of an oxidizer, and degrading the contaminant through a reaction of the contaminant, the composition, and the oxidizer.

Other systems, methods, features, and advantages of the disclosed compositions and methods will be or will become apparent to one with skill in the art upon examination of the following drawings and detailed description. It is intended that all such additional systems, methods, features, and advantages be included within this description, be within the scope of the present invention, and be protected by the accompanying claims.

DETAILED DESCRIPTION

In accordance with the purpose(s) of this disclosure, as embodied and broadly described herein, embodiments, in one aspect, relate to compositions including polyoxometalate/cationic silica (POM/(Si/ZO$_2$)$^+$) materials. Another aspect relates to compositions including POM/(Si/ZO$_2$)$^+$ materials, at least one copper (II) salt with weakly bound counter anions, and transition metal nitrates. An additional aspect relates to compositions having POM/(Si/ZO$_2$)$^+$ materials, copper (II) salts with weakly bound counter anions, and transition metal nitrates immobilized on anionic silica. Each of these embodiments can be included in coatings, topical skin protectants, fabrics, etc.

As indicated hereinabove, an embodiment of the invention includes compositions having at least one POM having the general formula of $[A][V_kMo_mW_nNb_oTa_pM_qX_rO_s]$ bound to cationic silica (e.g., (Si/(ZO$_2$)$^+$). "A" is at least one counterion, which can include, but is not limited to, alkali metal cations, alkaline earth metal cations, ammonium cations, quaternary ammonium cations, d-block cations, f-block cations, or combinations thereof. "M" is at least one element selected from d-block elements having at least one d-electron and f-block elements having at least one f-electron, except for vanadium, molybdenum, tungsten, niobium, or tantalum. "X" is at least one element selected from p-block elements, d-block elements, or f-block elements, except for oxygen. In addition, "k" can range from 0 to 30, "m" can range from 0 to 160, "n" can range from 0 to 160, "o" can range from 0 to 30, "p" can range from 0 to 10, "q" can range from 0 to 30, "r" can range from 0 to 30, "s" is sufficiently large that the negative charge on the POM unit, $[V_kMo_mW_nNb_oTa_pM_qX_rO_s]$, is greater than zero. Further, the sum of k, m, n, o, and p is greater than or equal to four; and the sum of k, m, and q is greater than zero.

In another embodiment, the POM has the formula $[X^{g+}V_bM^{h+}_cZ_{12-b-c}O_{40}]^{u-}[A]$. "X" is at least one p-, d-, or f-block element, where "g+" is the charge of X. "M" is at least one element selected from d-block elements having at least one d-electron and f-block elements having at least one f-electron, where "M" is not vanadium and "h+" is the charge of "M". "Z" is at least one element selected from tungsten, molybdenum, niobium, or a combination thereof. In addition, "b" is from 0 to 6; "c" is from 0 to 6, wherein the sum of "b" and "c" is greater than or equal to one; "u" is greater than 3. "A" is a counterion as described above. An example of a POM having this formula includes, but is not limited to, Na$_7$AlMn$_3$VW$_{10}$O$_{39}$.

In another embodiment, the POM has the formula $[X^{g+}V_bZ_{12-b}O_{40}]^{u-}[A]$. "X" is at least one element selected from phosphorus, silicon, aluminum, boron, zinc, cobalt, or iron. "Z" is at least one element selected from tungsten, molybdenum, niobium, or a combination thereof. In addition, "b" is from 1 to 6; and "u" is greater than 3. Exemplary POMs having this formula include, but are not limited to, Li$_5$PVW$_{11}$O$_{40}$, Na$_5$PVMo$_{11}$O$_{40}$, Ag$_6$PV$_3$Mo$_9$O$_{40}$, and Ag$_8$CoVW$_{11}$O$_{40}$.

In another embodiment, the POM has the formula $[X^{g+} M^{h+}{}_c Z_{12-c} O_{40}]^{u-}[A]$. "X" is at least one element selected from at least one phosphorus, silicon, aluminum, boron, zinc, cobalt, or iron. "Z" is at least one element selected from tungsten, molybdenum, niobium, or a combination thereof. "M" is at least one element selected from d-block elements having at least one d-electron and f-block elements having at least one f-electron. In addition, "c" is from 1 to 6; and "u" is greater than 3. Exemplary POMs having this formula include, but are not limited to, $K_4PFe^{III}W_{11}O_{39}$, $Na_5SiFe^{III}W_{11}O_{40}$, $Na_6AlFe^{III}W_{11}O_{40}$, and $Na_7ZnFe^{III}W_{11}O_{40}$.

In another embodiment, the POM has the formula $[X^{i+}{}_2 V_u M^{j+}{}_v Z_{18-u-v} O_{62}]^{w-}[A]$. "X" is at least one element selected from p-block elements, d-block elements, or f-block elements and "i+" is the charge of "X". "M" is at least one element selected from d-block elements having at least one d-electron and f-block elements having at least one f-electron, wherein "M" is not vanadium and "j+" is the charge of "M." "Z" is tungsten, molybdenum, niobium, or a combination thereof. In addition, "u" is from 0 to 9; "v" is from 0 to 9, wherein the sum of "u" and "v" is greater than or equal to one; "w" is greater than or equal to 4. An exemplary POM having this formula includes, but is not limited to, $Na_7P_2VFe^{III}{}_2W_{12}O_{59}$.

In another embodiment, the POM has the formula $[X^{i+}{}_2 V_u Z_{18-u} O_{62}]^{w-}[A]$. "X" is at least one element selected from phosphorus, sulfur, silicon, aluminum, boron, zinc, cobalt, or iron. "Z" is at least one element selected from tungsten, molybdenum, niobium, or a combination thereof. In addition, "u" is from 1 to 9; and "w" is greater than or equal to 4. Exemplary POMs having this formula include, but are not limited to, $K_9P_2V_3W_{15}O_{62}$ and $K_7S_2V_3W_{15}O_{62}$.

In another embodiment, the POM has the formula $[X^{i+}{}_2 M^{j+}{}_v Z_{18-v} O_{62}]^{w-}[A]$. "X" is at least one element selected from phosphorus, sulfur, silicon, aluminum, boron, zinc, cobalt, or iron. "Z" is at least one element selected from tungsten, molybdenum, niobium, or a combination thereof. "M" is at least one element selected from d-block elements having at least one d-electron and f-block elements having at least one f-electron. In addition, "v" is from 1 to 9; and "w" is greater than or equal to 4. Exemplary POMs having this formula include, but are not limited to, $Na_9P_2Fe^{III}{}_3W_{15}O_{59}$ and $Na_9S_2Fe^{III}{}_3W_{15}O_{59}$.

In another embodiment, the POM has the formula $[YV_x Z_{12-x} O_{40}][A]$. "Y" is at least one element selected from phosphorus, silicon, or aluminum. "Z" is at least one element selected from tungsten or molybdenum. In addition, "x" is from 1 to 6. "A" is a counterion. In one embodiment, "Y" is phosphorus and "Z" is molybdenum. In one embodiment, "Y" is phosphorus and "Z" is tungsten. In one embodiment, "Y" is silicon and "Z" is molybdenum. In one embodiment, "Y" is silicon and "Z" is tungsten. In one embodiment, "Y" is aluminum and "Z" is tungsten. In one embodiment, "Y" is aluminum and "Z" is molybdenum. An exemplary POM includes, but is not limited to, $Na_5PV_2Mo_{10}O_{40}$.

Cationic silica includes, but is not limited to, cationic metal or nonmetal oxide coated colloidal silica particles ($(Si/ZO_2)^+$), where "Si" is silicon, "Z" can be a metal or a nonmetal, and "O" is oxygen. "Z" includes metals such as, but not limited to, zirconium, aluminum, iron, copper, titanium, magnesium, cerium and chromium. The metal oxide silica surface functions as a cationic domain for the negatively charged POMs to bond. Not intending to be bound by any particular theory, the silica and POM can interact synergistically to enhance the selectivity and catalytic capability of the POM/$(Si/ZO_2)^+$ materials. By virtue of their compositions, these materials are completely stable to oxidative degradation and can be also rendered stable to hydrolytic degradation.

Another embodiment of the invention includes compositions having POM/$(Si/ZO_2)^+$ materials, copper (II) salts with weakly bound counter anions, and transition metal nitrates.

The anions of the copper (II) salt can be any known anion or large hydrophobic "low-charge" counterions. The anions can include, but are not limited to, weakly bound anions such as perchlorate, trifluoromethanesulfonate (commonly known as "triflate"), and tetrafluoroborate.

The transition metal nitrate can include transition metals such as, but not limited to, iron (II), cobalt (II), nickel (II), and copper (II). In addition, the transition metal cations in the transition metal nitrate can be replaced with soluble nitrate salt such as, but not limited to, tetraethylammonium (TEA) or tetra-n-butylammonium (TBA).

Still another embodiment of the invention includes compositions having POM/$(Si/ZO_2)^+$ materials, copper (II) salts having weakly bound counter anions, and transition metal nitrates immobilized (e.g., bonded and/or grafted) on anionic silica.

The anionic silica includes negatively charged amorphous silica and silica gel, for example. The surface of the anionic silica functions as a support for transition metals of the transition metal nitrates.

An exemplary mixture of the present invention includes compositions having a combination of: POM/$(Si/MO_2)^+$; copper (II) triflate, copper (II) perchlorate, copper (II) tetrafluoroborate, or combinations thereof; and/or copper (II) and/or iron (II) nitrate, for example.

Some compositions are effective at degrading contaminants such as warfare agents (e.g., chemical and/or biological warfare agents). Not intending to be bound by any particular theory, embodiments of the invention may be effective as catalysts with respect to the oxidation of chemical and/or biological warfare agents.

In this regard, Tables 1, 2, and 3 describe results obtained by allowing acetaldehyde, 2-chloroethyl ethyl sulfide (CEES), and tetrahydrothiophene (THT) to be oxidized by dioxygen in air while in the presence of the compositions listed in Tables 1, 2, and 3 respectively. In general, these compositions have demonstrated to be effective catalysts for oxidation of acetaldehyde, CEES, and THT using dioxygen as the terminal oxidant.

In general, about 20 to 40 milligrams (mg) of the POM or POM-modified silica (POM/(Si/$AlO_2$)) was weighed out into 20-milliliter (mL) vials and was suspended in 3.4 mL of hexane. After stirring for about 1 to 20 minutes, 0.068 mL (0.68 mmol), of trifluoroethanol (GC internal standard) and 0.025 mL (0.56 mmol) of $CH_3CHO$ were added to a vial fitted with a PTFE septum via syringe. The reaction was monitored for 40 hours at 25° C. The results are shown in Table 1.

TABLE 1

Aerobic Oxidation of Acetaldehyde in Hexane by Silica-supported Catalysts[a]

| Catalyst[b] | POM (mmol)[c] | % conv.[d] | % yield[e] | TOF[f] | TON[g] |
|---|---|---|---|---|---|
| (Si/AlO$_2$)Cl[h] | 0 | 0 | 0 | 0 | 0 |
| Na$_6$V$_{10}$O$_{28}$ (Na$_6$2)[i] | 0.12 | 0 | 0 | 0 | 0 |
| Na$_5$PV$_2$Mo$_{10}$O$_{40}$ (Na$_5$3)[f] | 0.18 | 55 | 42 | 0 | 1.3 |
| K$_9$Fe$_3$(A-PW$_9$O$_{34}$)$_2$ (K$_9$1)[f] | 0.57 | 2 | 2 | 0 | 0 |
| K$_{12}$Fe(OH$_2$)$_2$Fe$_2$(P$_2$W$_{15}$O$_{56}$)$_2$ (K$_{12}$4) | 0.18 | 2 | 2 | 0 | 0 |
| Na$_5$2/(Si/AlO$_2$)[i] | 0.002 | 14 | 14 | 1 | 40 |
| Na$_4$3/(Si/AlO$_2$)[i] | 0.002 | 11 | 10 | 0.8 | 33 |

TABLE 1-continued

Aerobic Oxidation of Acetaldehyde in
Hexane by Silica-supported Catalysts[a]

| Catalyst[b] | POM (mmol)[c] | % conv.[d] | % yield[e] | TOF[f] | TON[g] |
|---|---|---|---|---|---|
| $K_8 1/(Si/AlO_2)^i$ | 0.001 | 14 | 14 | 3 | 131 |
| $K_{11} 4/(Si/AlO_2)^i$ | 0.0004 | 15 | 15 | 5.5 | 220 |

[a]General conditions: 0.56 mmol (0.160 M) of $CH_3CHO$, catalyst (quantities given in the second column), 1 atm of air, 0.68 mmol (0.194 M) trifluoroethanol (internal standard) were stirred in 3.5 mL hexane at 25° C. for 40 h.;
[b]no product was observed in the absence of POM, $(Si/AlO_2)$ or POM/$(Si/AlO_2)$;
[c]mmol of total POM present in the catalyst during turnover;
[d]% conversion = (moles of $CH_3CHO$ consumed/moles of initial $CH_3CHO$) × 100;
[e]% yield = (moles of $CH_3COOH$/moles of initial $CH_3CHO$) × 100;
[f]turnover frequency (TOF) = turnovers/reaction time;
[g]turnovers (TON) = (moles of $CH_3COOH$/moles of POM);
[h]cationic silica (Bindzil CAT ®);
[i]$1 = [(Fe^{III}(OH_2)_2)_3(A-PW_9O_{34})_2]^{9-}$, $2 = V_{10}O_{28}^{6-}$, $3 = PV_2Mo_{10}O_{40}^{5-}$, $4 = [Fe(OH_2)_2Fe_2(P_2W_{15}O_{56})_2]^{12-}$ In a typical experiment, 15-25 mg of the POM-modified silica (POM/(Si/AlO$_2$)) was weighed out into 20-mL vials and was suspended in 1.0 mL of CH$_3$CN. A 0.5-mL aliquot (37.5 mmol total Cu(II)) of the optimized Cu(OTf)$_2$/Cu(NO$_3$)$_2$ solution and 0.876 mmol of 1,3-dichlorobenzene (GC internal standard) were placed into the vial containing the POM/(Si/AlO$_2$). The total volume was adjusted to 2.395 mL, and the vial was sealed and fitted with a PTFE septum. After the solution was stirred for 1-20 min, 0.105 mL of CEES was added to initiate the reaction. Air access to the mixture was provided through a needle in the cap. The reaction was monitored for 20 hours at 25° C.

The results are shown in Table 2. In particular, the treatment of CEES with some embodiments of the present invention resulted in more than 100 turnovers (i.e., moles of minimally toxic 2-chlorethyl ethyl sulfoxide (CEESO) product produced per mole of POM) after 10 minutes at ambient temperature, and more than 200 turnovers (i.e., moles of CEES produced per mole of POM) after 40 hours at ambient temperature.

TABLE 2

Aerobic Oxidation of CEES in acetonitrile by Silica-supported Catalysts[a]

| Catalyst[b] | POM (mmol)[c] | % conv.[d] | % yield[e] | TOF[f] | TON[g] |
|---|---|---|---|---|---|
| Cu(NO$_3$)$_2$/Cu(OTf)$_2$ (1)[h] | 0 | 56 | 56 | — | — |
| (Si/AlO$_2$)Cl[i] | 0 | 0 | 0 | 0 | 0 |
| TBA$_6$V$_{10}$O$_{28}$ (TBA$_6$2) | 0.003 | 0 | 0 | 0 | 0 |
| TBA$_5$PV$_2$Mo$_{10}$O$_{40}$ (TBA$_5$3) | 0.0035 | 2.5 | 2.4 | 0.3 | 6 |
| TBA$_6$Fe$_3$PW$_9$O$_{37}$ (TBA$_6$4) | 0.004 | 0 | 0 | 0 | 0 |
| TBA$_9$Fe$_3$(A-PW$_9$O$_{34}$)$_2$ (TBA$_9$5) | 0.004 | 0 | 0 | 0 | 0 |
| TBA$_{12}$Fe(OH$_2$)$_2$Fe$_2$(P$_2$W$_{15}$O$_{56}$)$_2$ (TBA$_{12}$6) | 0.002 | 0 | 0 | 0 | 0 |
| Na$_6$2[j] | 0.005 | 0 | 0 | 0 | 0 |
| Na$_5$3[j] | 0.005 | 2 | 2 | 0.17 | 3.5 |
| K$_6$4[j] | 0.004 | 0 | 0 | 0 | 0 |
| K$_9$5[j] | 0.005 | 0 | 0 | 0 | 0 |
| K$_{12}$6[j] | 0.005 | 0 | 0 | 0 | 0 |
| 1/TBA$_6$2[k] | 0.003 | 56 | 56 | 0 | 0 |
| 1/TBA$_5$3[k] | 0.0035 | 56 | 56 | 0 | 0 |
| 1/TBA$_6$4[k] | 0.004 | 81 | 81 | 8.9 | 177 |
| 1/TBA$_9$5[k] | 0.002 | 57 | 57 | 0 | 0 |
| 1/TBA$_{12}$6[k] | 0.0022 | 56 | 56 | 0 | 0 |
| 1/Na$_6$2/(Si/AlO$_2$)[l] | 0.0009 | 59 | 58 | 0 | 0 |
| 1/Na$_4$3/(Si/AlO$_2$)[l] | 0.0007 | 67 | 66 | 41 | 827 |
| 1/K$_6$4/(Si/AlO$_2$)[l] | 0.0011 | 94 | 94 | 38 | 752 |
| 1/K$_8$5/(Si/AlO$_2$)[l] | 0.0006 | 81 | 80.0 | 58 | 1167 |
| 1/K$_{11}$6/(Si/AlO$_2$)[l] | 0.0004 | 56 | 56 | 0 | 0 |

[a]General conditions: 0.875 mmol (0.35 M) of CEES, catalyst (quantity given in column 2), 1 atm of air, 0.876 mmol (0.35 M) of 1,3-dichlorobenzene (internal standard) were stirred in 2.5 mL of acetonitrile at 25° C. for 20 h;
[b]no product was observed in the absence of POM, (Si/AlO$_2$) or POM/(Si/AlO$_2$);
[c]mmol of total POM present in the catalyst during turnover;
[d]% conversion = (moles of CEES consumed/moles of initial CEES) × 100;
[e]% yield = (moles of CEESO/moles of initial CEES) × 100;
[f]turnover frequency = turnovers/reaction time;
[g]turnovers = (moles of CEESO/moles of POM);
[h](1) = 15 mM Cu(NO$_3$)$_2$ + 22.5 mM Cu(OTf)$_2$;
[i]cationic silica (Bindzil CAT ®[i]; 0.015 g suspended in solution);
[j]$2 = V_{10}O_{28}^{6-}$, $3 = PV_2Mo_{10}O_{40}^{5-}$, $4 = [Fe_3PW_9O_{37}]^{6-}$, $5 = [(Fe^{III}(OH_2)_2)_3(A-\alpha-PW_9O_{34})_2]^{9-}$, $6 = [Fe(OH_2)_2Fe_2(P_2W_{15}O_{56})_2]^{12-}$;
[k]homogeneous catalysis (both 1 and POM soluble);
[l]heterogeneous catalysis (POM bound to (Si/AlO$_2$)$^{n+}$ as insoluble powder suspended in a solution of 1).

The POM-modified silica (POM/(Si/AlO$_2$)) (15-25) mg was weighed out into 20-mL vials and suspended in 2.3 mL of CH$_3$CN. After stirring for 1-20 min, 0.100 mL (0.876 mmol) of 1,3-dichlorobenzene (GC internal standard) and 0.087 mL (0.99 mmol) of THT are added into a vial fitted with a PTFE septum via syringe. Air access during the experiment is provided through the needle in the cap. The reaction is monitored for 120 hours at 75° C. The results are shown in Table 3.

TABLE 3

Selective Catalytic Aerobic Oxidation of Tetrahydrothiophene to
Tetrahydrothiophene Oxide (THTO) Under Ambient Conditions.[a]

| Catalyst[b] | POM (mmol)[c] | % conv[d] | % yield[e] | TOF[f] | TON[g] |
|---|---|---|---|---|---|
| (Si/AlO$_2$)Cl[h] | 0 | 0 | 0 | 0 | 0 |
| Fe(Si/AlO$_2$)[i] | 0.0008[j] | 1.5 | 1.5 | 0 | 1.8 |
| TBA$_9$Fe$_3$(A-PW$_9$O$_{34}$)$_2$(TBA$_9$1) (homogeneous reaction) | 0.0045 | 2.5 | 2.5 | 0 | 2.2 |
| K$_8$1/(Si/AlO$_2$)[k] | 0.0045 | 28 | 28 | 0.5 | 60 |

[a]General conditions: 0.99 mmol (0.397 M) of THT, catalyst (amount given in column 2), 1 atm of air, 0.875 mmol (0.35 M) dichlorobenzene (internal standard) were stirred in 2.5 mL of acetonitrile at 75° C. for 120 h.;
[b]no product was observed in the absence of POM, (Si/AlO$_2$)$^{n+}$ or POM/(Si/AlO$_2$);
[c]mmol of total POM present in the catalyst during turnover;
[d]% conversion = (moles of THT consumed/moles of initial THT) × 100;
[e]% yield = (moles of THTO/moles of initial THT) × 100;
[f]turnover frequency = turnovers/reaction time (120 h);
[g]turnovers = (moles of THTO/moles of POM);
[h]cationic silica (Bindzil CAT ®)$^3$;
[i]Fe(III)-coated Bindzil CAT ®;
[j]mmol of Fe$_2$(SO$_4$)$_3$ (no POM present);
[k]$1 = [(Fe^{III}_3)(A-PW_9O_{34})_2]^{9-}$.

Compositions of the present invention are capable of degrading a single contaminant or multiple contaminants in an environment. The term "environment" as used herein refers to any media that contains at least one contaminant. For example, in one embodiment, the environment may comprise a liquid phase. In another embodiment, the environment may comprise a gas phase.

The term "degrade", "degrading", or "degradation" refers, but is not limited to, the degradation of the contaminant, the conversion of the contaminant into another compound that is either less toxic or nontoxic, or the adsorption of the contaminant by the compositions of the present invention. The compositions may be able to degrade the contaminant by a number of different mechanisms. For example, the compositions of the present invention can aerobically oxidize the contaminant.

Contaminants that can be degraded by using compositions of the present invention include, but are not limited to, chemical warfare agents, biological warfare agents, or combinations thereof. Exemplary chemical warfare agents include mustard gas and sarin, while an exemplary biological warfare agent includes anthrax.

Some of the chemical warfare agents and biological warfare agents disclosed in Marrs, Timothy C.; Maynard, Robert L.; Sidell, Frederick R.; *Chemical Warfare Agents Toxicology and Treatment*; John Wiley & Sons: Chichester, England, 1996; Compton, James A. F.; *Military Chemical and Biological Agents Chemical and Toxicological Properties*; The Telford Press: Caldwell, N.J., 1988; Somani, Satu M.; *Chemical Warfare Agents*; Academic Press: San Diego, 1992, which are incorporated herein by reference in their entirety, may be degraded by embodiments of the invention.

Furthermore, contaminants that can be degraded by using embodiments of the present invention generally include, but are not limited to, the following: aldehydes, aliphatic nitrogen compounds, sulfur compounds, aliphatic oxygenated compounds, halogenated compounds, organophosphate compounds, phosphonothionate compounds, phosphorothionate compounds, arsenic compounds, chloroethyl compounds, phosgene, cyanic compounds, or combinations thereof. In one embodiment, the contaminant is acetaldehyde, methyl mercaptan, ammonia, hydrogen sulfide, diethyl sulfide, diethyl disulfide, dimethyl sulfide, dimethyl disulfide, trimethylamine, styrene, propionic acid, n-butyric acid, n-valeric acid, iso-valeric acid, pyridine, formaldehyde, 2-chloroethyl ethyl sulfide, carbon monoxide, or combinations thereof.

Compositions of the present invention are typically used in the presence of an oxidizer to degrade a contaminant from the environment. An example of an oxidizer includes, but is not limited to, dioxygen. In a preferred embodiment, dioxygen present in the air is used as the oxidizer.

Compositions of the present invention can be incorporated into a suitable material in order to facilitate the protection and/or degradation of a contaminant. The materials may include, for example, carriers, coatings, powders, and/or fabrics. A "material" as used herein refers to media that incorporates one or more of the topical compositions of the present invention. In addition, the compositions of the present invention can be incorporated into air filters, water filters, and the like.

Some compositions can be incorporated into the material using techniques known in the art. In one embodiment, when the material is a topical carrier, powder, or coating, the mixtures are directly added to and admixed with the material. In one embodiment, the components of the compositions can be incorporated sequentially into the material. In another embodiment, the material is contacted with compositions comprising the mixtures and a solvent. The compositions can be soluble, partially soluble, or insoluble in the solvent, depending upon the components of the mixture and the solvent selected. In one embodiment, the solvent is water. In another embodiment, the solvent can be an organic solvent. Examples of solvents useful in embodiments of the present invention include, but are not limited to, acetonitrile, toluene, carbon dioxide, xylenes, 1-methyl-2-pyrrolidinone, or fluorinated media such as perfluoropolyether compounds.

The amount of each component incorporated into the material varies, depending partly upon the contaminant to be degraded and the material that is selected. There is little restriction on the amount of each component that can be incorporated into the material. In one embodiment, the amount of the composition incorporated in the material is from 0.1 to 95% by weight of the composition. In one embodiment, the lower limit of the composition by weight maybe 0.05, 0.1, 0.5, 1.0, 2.0, 5.0, 10, 15, 20, 25, 30, 35, 40, 45, or 50%, and the upper limit maybe 30, 40, 50, 60, 70, 80, 90, or 95%. In one embodiment, when the material is a topical carrier, the composition is from 1 to 50% by weight of topical composition.

Compositions of the present invention can be used in a wide variety of topical carriers. Suitable topically acceptable pharmaceutical carriers are those which typically are used in the topical application of pharmaceuticals and cosmetics. Examples of such carriers include, but are not limited to, lotions, creams, ointments, and gels. In some applications, topical carriers can be referred to as barrier creams and topical skin protectants. Any of the topical carriers disclosed in U.S. Pat. No. 5,607,979, to McCreery, can be used in some of the embodiments of the present invention, which is incorporated by reference in its entirety. In one embodiment, the topical carrier comprises a perfluorinated media (e.g., a polymer or a mixture of polymers). In another embodiment, the topical carrier comprises perfluoropolyether compounds. An example of a perfluoropolyether (PFPE) compound useful in the present invention has the general formula $CF_3O[—CF(CF_3)CF_2O—]_x(—CF_2O—)_yCF_3$. Examples of PFPE media include Fluorolink®, Galden®, and Fomblin®, for example, commercially available from the Ausimont Montedison Group. In one embodiment, the topical carrier comprises a perflourinated polymer and one or more unfluorinated polymers or compounds. In another embodiment, the topical carrier comprises a perfluoropolyether and one or more unfluorinated polyethers.

In one embodiment, the topical carrier may further contain saturated or unsaturated fatty acids such as stearic acid, palmitic acid, oleic acid, palmito-oleic acid, cetyl or oleyl alcohols, stearic acid, fluorinated acids, fluorinated alcohols, or combinations thereof. The cream may also optionally contain one or more surfactants, such as a nonionic surfactant.

A wide variety of powders and coatings (e.g., thermoplastics and thermosettings) known in the art can be used as the material in embodiments of the present invention. In one embodiment, the powder comprises activated carbon. In another embodiment, the powder comprises cationic metal oxide nanoparticles.

Almost any fabric can be developed to include one or more of the compositions. In one embodiment, fabrics used to prepare garments, draperies, carpets, and upholstery can be used and articles made from them are a part of this invention. In another embodiment, the fabric can be a knit or non-woven fabric. Useful fibers include, but are not limited to, polyamide, cotton, polyacrylic, polyacrylonitrile, polyester, polyvinylidine, polyolefin, polyurethane, polyurea, polytetrafluoroethylene, carbon cloth, or combinations thereof. In still another embodiment, the fabric is prepared from cotton, polyacrylic, or polyacrylonitrile. In still another embodiment, the fabric is prepared from a cationic fiber. In another embodiment, the fabric comprises (1) a 50/50 blend of nylon-6, 6 and cotton or (2) stretchable carbon blended with polyurethane or polyurea.

Further, any cellulosic fiber can incorporate the compositions of the present invention. Examples of useful cellulosic fibers include, but are not limited to, wood or paper.

In one embodiment, when the material is a fabric or cellulosic fiber, the material includes from about 0.1 to about 20% by weight composition and from initially about 80 to about 99.9% by weight water, preferably from about 0.3 to about 15% by weight composition and initially 85 to 99.7% by weight water. Generally, the fabric or cellulosic fiber is dipped or immersed into the mixture containing the composition from several hours up to days at a temperature of from about 0° C. to 100° C., preferably for 2 hours to 2 days at from about 25° C. to 80° C. In another embodiment, the composition can be admixed with a resin or adhesive, and the resultant adhesive is applied to the surface of, or admixed with, the fabric or cellulosic fiber.

Typically, once the material has been contacted with the composition, the composition is dried in order to remove residual solvent. In one embodiment, the mixture is heated from about 0° C. to 220° C. at or below atmospheric pressure, preferably from about 25° C. to 100° C. In another embodiment, the composition is dried in vacuo (i.e., less than or equal to about 10 torr).

In another embodiment, when the material is a fabric or cellulosic fiber, the composition can be incorporated into the fabric or cellulosic fiber by depositing the composition on the surface of an existing fabric or cellulosic fiber, covalently bonding the components of the composition to the fibers of the fabric or cellulosic fiber, impregnating or intimately mixing the composition with the fabric or cellulosic fiber, electrostatically bonding the components of the composition to the fabric or cellulosic fiber, or datively bonding the components of the composition to the fabric or cellulosic fiber.

Compositions of the present invention have a number of advantages over the prior art decontaminants. One advantage is that compositions of the present invention can catalytically degrade a contaminant from the environment starting within milliseconds of contact and can degrade the contaminant for extended periods of time, ranging from several days to indefinitely. Another advantage is that some compositions can render the material more water-resistant and increase the surface area of the material. Finally, when the material is a fabric or cellulosic fiber, the composition can enhance the dyeability, light fastness, color fastness, and weaving properties of the fabric or cellulosic fiber.

General Considerations

Materials

All reagents except cationic silica Bindzil CAT® and Cu(II) trifluoromethanesulfonate $(Cu(OTf)_2).6H_2O$ used in the examples were obtained from Aldrich Chemical Company, and were used without further purification. The following reagents were used in the examples (the purity of the reagent is in parenthesis): CEES (98%), acetonitrile (HPLC grade), hexane (99%) 1,3-dichlorobenzene (98%), acetaldehyde (99%), 2,2,2-trifluoroethanol (99.5%), $Cu(NO_3)_2 \cdot 2.5H_2O$ (99%). Bindzil CAT® (aqueous suspension of 10% $SiO_2$ and 4% $Al_2O_3$) was obtained from Akzo Nobel Company. $Cu(OTf)_2.6H_2O$ (99%) was purchased from Alfa Aesar Company and both used as received.

Synthesis of $K_9(Fe((OH_2)_2)_3)(A-\alpha-PW_9O_{34})_2$ $A-Na_9PW_9O_{34}.7H_2O$ was prepared by the literature method [Massart, R.; Contant, R.; Fruchart, Jean-Marc; Ciabrini, Jean-Pierre; and Fournier, M. *Inorg. Chem.* 1977, 16, 2916-2921; Domalle, P. *Inorg. Synth.* 1990, 27, 96-104].

$K_9(Fe((OH_2)_2)_3)(A-\alpha-PW_9O_{34})_2$ was prepared by the following procedure. Solid $Fe(NO_3)_3.9H_2O$ (3.2 g, 8 mmol) was dissolved in 100 mL of water and heated to 65° C. (pH of the solution was 1.75). To this solution solid $A-Na_9PW_9O_{34}.7H_2O$ (10 grams (g), ca. 3.7 mmol) was added. The mixture was stirred for 60 minutes at 55° C. to form a dark greenish-brown solution to which KCl (25 g) was added. The resulting precipitate (ca. 8 g) was separated by filtration, re-dissolved in a minimal amount of 50° C. water and the solution filtered to remove any insoluble material. The filtrate was cooled to 5° C. overnight to afford 6 g of greenish-orange crystals (yield 60%). Diffuse-reflectance-fourier-transform-infrared (5% sample in KBr, 1200-400 $cm^{-1}$): 1080 (s), 1058 (s, sh), 953 (s), 881 (m), 799 (s), 752 (s, sh), 595 (w), and 517 (w). Anal. Calcd. for $H_{46}Fe_3K_9O_{94}P_2W_{18}$: H, 0.85; Fe, 3.08; K, 6.47; P, 1.14; W, 60.82. Found: H, 0.88; Fe, 3.13; K, 6.53; P, 1.17; W, 59.09. Magnetic susceptibility: $\mu_{eff}$=6.1 $\mu_B$/mol at 296K. MW: 5441.

Synthesis of Additional Polyoxometalates

The following POMs listed in Table 1 were prepared by literature procedures (the entry number in Table 1 and the bibliographical information are in parenthesis):

$Na_6V_{10}O_{28}$ (Entry 2; Johnson, G. K.; Murmann R. K. in D. Shriver (Ed.), *Inorganic Syntheses* 1979, 19, 140, Wiley, N.Y.).

$Na_5PV_2Mo_{10}O_{40}$ (Entry 3; Pettersson, L; Andersson, I.; Selling, A.; Grate, G. H., *Inorg. Chem.* 1994, 33, 982-993).

$K_{12}Fe(OH_2)_2Fe_2(P_2W_{15}O_{56})_2$ (Entry 5; Zhang, X.; Chen, Q.; Duncan, D. C.; Campana, C.; Hill, C. L., *Inorg. Chem.* 1997, 36, 4208-4215.

The following POMs listed in Table 2 were prepared by the following experimental procedures:

$TBA_6V_{10}O_{28}$ (Entry 3): 1.0 g (0.0007 mmol) of $Na_6V_{10}O_{28}$ was dissolved in 80 mL of deionized water. To this solution TBABr (6.35 g; 0.0049 mmol) dissolved in 20 mL of deionized water was added. The solution was stirred for 30 min and the resulting orange precipitate of $TBA_6V_{10}O_{28}$ was separated by filtration.

$TBA_5PV_2Mo_{10}O_{40}$ (Entry 4): 1.0 g (0.0007 mmol) of $Na_5PV_2Mo_{10}O_{40}$ was dissolved in 80 mL of deionized water. To this solution TBABr (6.35 g; 0.0049 mmol) dissolved in 20 mL of deionized water was added. The solution was stirred for 30 min and the resulting orange precipitate of $TBA_5PV_2Mo_{10}O_{40}$ was separated by filtration.

$TBA_6Fe_3PW_9O_{37}$ (entry 5; Zang, X.; Hill, C. L., Unpublished data, 1998.)

$TBA_9(Fe((OH_2)_2)_3)(A-\alpha-PW_9O_{34})_2$ (Entry 6): 1 g (0.00018 mmol) of $K_9(Fe((OH_2)_2)_3)(A-\alpha-PW_9O_{34})_2$ was dissolved in 80 mL of deionized water. To this solution TBABr (2.32 g; 0.0018 mmol) dissolved in 20 mL of deionized water was added. The solution was stirred for 30 min and resulting pale yellow precipitate of $TBA_9(Fe((OH_2)_2)_3)(A-\alpha-PW_9O_{34})_2$ was separated by filtration.

$TBA_{12}Fe(OH_2)_2Fe_2(P_2W_{15}O_{56})_2$ (Entry 7): 1 g (0.0001 mmol) of $K_{12}Fe(OH_2)_2Fe_2(P_2W_{15}O_{56})_2$ was dissolved in 80 mL of deionized water. To this solution TBABr (1.81 g; 0.0014 mmol) dissolved in 20 mL of deionized water was added. The solution was stirred for 30 minutes (min), and the resulting greenish-yellow precipitate of $TBA_{12}Fe(OH_2)_2Fe_2(P_2W_{15}O_{56})_2$ was separated by filtration.

Preparation of the Catalyst Materials

In a typical preparation, a solution of the POM (0.25 g of $Na_6V_{10}O_{28}$, $Na_5PV_2Mo_{10}O_{40}$, $K_9(Fe((OH_2)_2)_3)(A-\alpha-PW_9O_{34})_2$, or $\alpha\beta\beta\alpha-Na_{12}(FeOH_2)_2Fe(P_2W_{15}O_{56})_2$ in 10 mL of deionized water) or a solution of (0.30 g of $TBA_6V_{10}O_{28}$, $TBA_5PV_2Mo_{10}O_{40}$, $TBA_9(Fe((OH_2)_2)_3)(A-\alpha-PW_9O_{34})_2$, or $\alpha\beta\beta\alpha-TBA_{12}(FeOH_2)_2Fe_2(P_2W_{15}O_{56})_2$ in 10 mL of acetonitrile) was added to a suspension of $(Si/AlO_2)Cl$ (Akzo Nobel Bindzil CAT®, 10 g). The resulting mixture was stirred for 3 hours (h) at 25° C. and then heated to 80° C. until the water was completely evaporated. The resulting powder was dried at 120° C. for 1 h, washed with three 10-mL portions of acetonitrile (with no loss of POM after the first wash), and dried again at 120° C. for 1 h. Elemental analysis, laser light scattering measurements, and infrared spectroscopy confirmed the purity of the material.

Preparation and Optimization of the Catalytic Activity of $Cu(OTf)_2/Cu(NO_3)_2$ Solutions A stock solution of 15 mM $Cu(NO_3)_2$ was prepared in 25-mL vials using anhydrous $CH_3CN$. The concentration of $Cu(OTf)_2$ was varied from 10 mM to 37.5 mM. The concentration of $Cu(NO_3)_2$ was kept constant in all reactions (15 mM). Aliquots (0.5 mL) of the $Cu(OTf)_2/Cu(NO_3)_2$ solution were placed in 20-mL vials and 0.876 mmol of 1,3-dichlorobenzene (GC internal standard) was added to each. The total volume of each solution was adjusted to 2.395 mL (4 significant figures justified) by addition of anhydrous $CH_3CN$, and each vial was sealed and fitted with a PTFE septum. After stirring for about 1-20 min, 0.100 mL of 2-chloroethyl ethyl sulfide (CEES) was added via syringe. Air access during the reaction was provided through the needle in the cap. Each reaction was stirred continuously and monitored for 20-24 hours, and aliquots were removed for GC analysis every 15 minutes. Importantly, the optimal ratio of $Cu(OTf)_2/Cu(NO_3)_2$ was subsequently used in all experiments. The $Cu(OTf)_2/Cu(NO_3)_2$ solution was evaluated for activity after catalysis (9 and 13 turnovers, respectively) and no change in activity was apparent. Blue-green crystals of $Cu(OTf)_2$ (identified by X-ray crystallography) were re-isolated in high yield after catalysis (aerobic CEES oxidation).

Instrumentation

The particle size distribution of the Bindzil CAT® and POM/(Si/AlO$_2$) was determined by photon correlation spectroscopy (PCS) using a Coulter N4 Plus instrument from Beckman-Coulter Company. The infrared spectra were recorded on a Nicolet 510 FT-IR spectrometer, and $^1H$ and $^{13}C$ NMR spectra were recorded on a Varian INOVA 400 MHz spectrometer. Oxidation products were identified and quantified by gas chromatography (GC, Hewlett Packard 5890 series gas chromatograph equipped with a flame ionization detector, 5% phenyl methyl silicone capillary column for CEES oxidation, or HP-FFAP column (high polarity nitroterephthalic acid modified polyethylene) for acetaldehyde oxidation, $N_2$ carrier gas, and a Hewlett Packard 3390A series integrator). Gas chromatography-mass spectrometry measurements were performed on a Hewlett Packard 5890 series II gas chromatograph connected to a Hewlett Packard 5971 mass selective detector. Elemental analyses were performed by Desert Analytics in Tucson, Ariz., USA.

It should be emphasized that the above-described embodiments of the disclosed compositions and methods, particularly, any "preferred" embodiments, are merely possible examples of implementations, and are merely set forth for a clear understanding of the principles disclosed herein. Many variations and modifications may be made to the above-described embodiment(s) without departing substantially from the spirit and principles of the invention. All such modifications and variations are intended to be included herein within the scope of this disclosure and the present invention and protected by the following claims.

Therefore, having thus described the invention, at least the following is claimed:

1. A composition for degrading a contaminant, comprising: a polyoxometalate(POM)/cationic silica material.

2. The composition of claim 1, further comprising:
a copper (II) salt having a weakly bound anion; and
a transition metal nitrate.

3. The composition of claim 2, wherein the transition metal nitrate is immobilized on anionic silica.

4. The composition of claim 2, wherein the copper (II) salt having a weakly bound anion is selected from the group consisting of: copper (II) perchlorate, copper (II) triflate, copper (II) tetrafluoroborate, and a combination thereof.

5. The composition of claim 2, wherein the transition metal nitrate is selected from the group consisting of: iron (III) nitrate, cobalt (II) nitrate, nickel (II) nitrate, and copper (II) nitrate.

6. The composition of claim 2, wherein the POM/cationic silica material is selected from the group consisting of: $Na_4PV_2Mo_{10}O_{40}{}^{5-}/(Si/AlO_2)$, $K_6[Fe_3PW_9O_{37}]^{6-}/(Si/AlO_2)$, and $K_8[(Fe^{III}(OH_2)_2)_3(A\text{-}\alpha\text{-}PW_9O_{34})_2]^{9-}/(Si/AlO_2)$; wherein the copper (II) salt having a weakly bound anion is $Cu(OTf)_2$; and wherein the transition metal nitrate is $Cu(NO_3)_2$.

7. The composition of claim 1, further comprising:
a copper (II) salt having a weakly bound anion; and
a soluble nitrate salt.

8. The composition of claim 7, wherein the copper (II) salt having a weakly bound anion is selected from the group consisting of: copper (II) perchlorate, copper (II) triflate, copper (II) tetrafluoroborate, and a combination thereof.

9. The composition of claim 7, wherein the transition metal nitrate is selected from the group consisting of: iron (III) nitrate, cobalt (II) nitrate, nickel (II) nitrate, and copper (II) nitrate.

10. The composition of claim 1, wherein the POM comprises a POM having the formula of $A[V_kMo_mW_nNb_oTa_pM_qX_rO_s]$ bound to cationic silica; wherein A is at least one counterion selected from the group consisting of: an alkali metal cations, an alkaline earth metal cations, an ammonium cations, a quaternary ammonium cations, a d-block cations, a f-block cations, and a combinations thereof; wherein M is at least one element selected from the group consisting of: a d-block elements having at least one d-electron and f-block elements having at least one f-electron, except for vanadium, molybdenum, tungsten, niobium, or tantalum; wherein X is at least one element selected from the group consisting of: a p-block elements, d-block elements, and a f-block elements, except for oxygen; wherein k can range from 0 to 30; wherein m can range from 0 to 160; wherein n can range from 0 to 160; wherein o can range from 0 to 30; wherein p can range from 0 to 10; wherein q can range from 0 to 30; wherein r can range from 0 to 30; wherein s is sufficiently large that the negative charge on the POM unit, $[V_kMo_mW_nNb_oTa_pM_qX_rO_s]$, is greater than zero; wherein the sum of k, m, n, o, and p is greater than or equal to four; wherein the sum of k, m, and q is greater than zero; and wherein A is at least one counterion selected from the group consisting of: an alkali metal cations, alkaline earth metal cations, an ammonium cations, a quaternary ammonium cations, d-block cations, f-block cations, and a combinations thereof.

11. The composition of claim 1, wherein the POM comprises, a POM having the formula $[X^{g+}V_bM^{h+}{}_cZ_{12-b-c}O_{40}]^{u-}[A]$, wherein X is at least one element selected from the group consisting of: p-block elements, a d-block elements, and a f-block elements; wherein g+ is the charge of X; wherein M is at least one element selected from the group consisting of: a d-block elements having at least one d-electron and f-block elements having at least one f-electron; wherein M is not vanadium; wherein h+ is the charge of M; wherein Z is at least one element selected from the group consisting of: tungsten, molybdenum, niobium, and combinations thereof; wherein b is from 0 to 6; wherein c is from 0 to 6; wherein the sum of b and c is greater than or equal to one; wherein u is greater than 3; and wherein A is at least one counterion selected from the group consisting of: alkali metal cations, an alkaline earth metal cations, an ammonium cations, a quaternary ammonium cations, a d-block cations, a f-block cations, and a combinations thereof.

12. The composition of claim 1, wherein the POM comprises, a POM having the formula $[X^{g+}V_bZ_{12-b}O_{40}]^{u-}[A]$; wherein X is at least one element selected from the group consisting of: phosphorus, silicon, aluminum, boron, zinc, cobalt, and iron; wherein g+ is the charge of X; wherein Z is at least one element selected from the group consisting of: tungsten, molybdenum, niobium, and a combination thereof; wherein b is from 1 to 6; wherein u is greater than 3; and wherein A is at least one counterion selected from the group consisting of: an alkali metal cations, an alkaline earth metal cations, an ammonium cations, a quaternary ammonium cations, a d-block cations, a f-block cations, and a combinations thereof.

13. The composition of claim 1, wherein the POM comprises, a POM having the formula $[X^{g+}M^{h+}{}_cZ_{12-c}O_{40}]^{u-}[A]$; wherein X is at least one element selected from the group consisting of: phosphorus, silicon, aluminum, boron, zinc, cobalt and iron; wherein g+ is the charge of X; wherein Z is at least one element selected from the group consisting of: tungsten, molybdenum, niobium, and a combination thereof; wherein M is at least one element selected from the group consisting of: a d-block element having at least one d-electron and f-block element having at least one f-electron; wherein c is from 1 to 6; wherein u is greater than 3; and wherein A is at least one counterion selected from the group consisting of: an alkali metal cation, an alkaline earth metal cation, an ammonium cation, a quaternary ammonium cation, a d-block cation, a f-block cation and a combination thereof.

14. The composition of claim 1, wherein the POM comprises, a POM having the formula $[X^{i+}{}_2V_uM^{j+}{}_vZ_{18-u-v}O_{62}]^{w-}[A]$; wherein X is at least one element selected from the group consisting of: a p-block elements, a d-block elements, and a f-block elements; wherein i+ is the charge of X; wherein M is at least one element selected from the group consisting of: a d-block elements having at least one d-electron and f-block elements having at least one f-electron; wherein M is not vanadium; wherein j+ is the charge of M; wherein Z is at least one element selected from the group consisting of: tungsten, molybdenum, niobium, and a combinations thereof; wherein u is from 0 to 9; wherein v is from 0 to 9; wherein the sum of u and v is greater than or equal to one; wherein w is greater than or equal to 4; and wherein A is at least one counterion selected from the group consisting of: an alkali metal cation, an alkaline earth metal cations, ammonium cation, quaternary ammonium cation, a d-block cation, a f-block cation, and combination thereof.

15. The composition of claim 1, wherein the POM has the formula $[X^{i+}{}_2V_uZ_{18-u}O_{62}]^{w-}[A]$ wherein X is at least one element selected from the group consisting of: phosphorus, sulfur, silicon, aluminum, boron, zinc, cobalt, and iron; wherein Z is at least one element selected from the group consisting of: tungsten, molybdenum, niobium, and a combination thereof; wherein i+ is the charge of X; wherein u is from 1 to 9; wherein w is greater than or equal to 4, and wherein A is at least one counterion selected from the group consisting of: an alkali metal cation, an alkaline earth metal cation, an ammonium cation, a quaternary ammonium cation, a d-block cation, a f-block cation, and a combination thereof.

16. The composition of claim 1, wherein the POM has the formula $[X^{i+}{}_2M^{j+}{}_vZ_{18-v}O_{62}]^{w-}[A]$, wherein X is at least one element selected from the group consisting of: phosphorus, sulfur, silicon, aluminum, boron, zinc, cobalt, and iron; wherein i+ is the charge of X; wherein Z is selected from the group consisting of: tungsten, molybdenum, niobium, and a combination thereof; wherein M is at least one a d-block element having at least one d-electron or f-block element having at least one f-electron; wherein v is from 1to 9; wherein w is greater than or equal to 4, and wherein A is at least one counterion selected from the group consisting of: an alkali metal cation, an alkaline earth metal cation, an ammonium cation, a quaternary ammonium cation, a d-block cation, a f-block cation, and a combination thereof.

17. The composition of claim 1, wherein the POM has the formula $[YV_xZ_{12-x}O_{40}][A]$, wherein Y is at least one element selected from the group consisting of: phosphorus, silicon, and aluminum; wherein Z is at least one element selected from the group consisting of: tungsten and molybdenum; wherein x is from 1 to 6, and wherein A is at least one counterion selected from the group consisting of: an alkali metal cation, an alkaline earth metal cation, an ammonium cation, a quaternary ammonium cation, a d-block cation, a f-block cation, and a combination thereof.

18. The composition of claim 1, wherein the POM comprises iron.

19. The composition of claim 1, wherein the cationic silica material comprises a metal oxide coated silica.

20. The composition of claim 19, wherein the metal of the metal oxide is chosen from the group consisting of: zirconium, aluminum, iron, copper, titanium, magnesium, cerium, and chromium.

21. The composition of claim 1, wherein the cationic silica material comprises a nonmetal oxide coated silica.

22. The composition of claim 1, wherein the POM/cationic silica material is selected from the group consisting of:
$K_8[(Fe^{III}(OH_2)_2)_3(A-PW_9O_{34})_2]^{9-}/(Si/AlO_2)$;
$Na_4PV_2Mo_{10}O_{40}{}^{5-}/(Si/AlO_2)$; $Na_5V_{10}O_{28}{}^{6-}/(Si/AlO_2)$;
$K_{11}[Fe(OH_2)_2Fe_2(P_2W_{15}O_{56})_2]^{12-}/(Si/AlO_2)$; and
$K_8[(Fe^{III}{}_3)(A-PW_9O_{34})_2]^{9-}/(Si/AlO_2)$.

23. A material for degrading a contaminant, comprising:
a material selected from the group consisting of: topical carriers, coatings, powders, and fabrics, wherein the material includes a composition selected from the group consisting of: the composition of claim 1, the composition of claim 2, the composition of claim 3, and or the composition of claim 4.

24. The material of claim 23, wherein the topical carriers are selected from the group consisting of: lotions, creams, ointments, gels, barrier creams, topical skin protectants, and combinations thereof.

25. The material of claim 23, wherein the fabric includes fibers selected from the group consisting of: polyamide fibers, cellulosic fibers, cotton fibers, polyacrylic fibers, polyacrylonitrile fibers, polyester fibers, polyvinylidine fibers, polyolefin fibers, polyurethane fibers, polyurea fibers, polytetrafluoroethylene fibers, carbon cloth fibers, and a combination thereof.

26. A method of degrading a contaminant, comprising:
providing the material of claim 23;
contacting the material with the contaminant in the presence of an oxidizer; and
degrading the contaminant through a reaction of the contaminant, the composition, and the oxidizer.

27. The method of claim 26, wherein degrading includes:
degrading the contaminant catalytically.

28. The method of claim 26, wherein degrading includes:
degrading the contaminant by aerobically oxidizing the contaminant.

29. The method of claim 26, wherein the contaminant is selected from the group consisting of: chemical warfare agents, biological warfare agents, and a combination thereof.

30. The method of claim 26, wherein the contaminant is selected from the group consisting of: aldehydes, aliphatic nitrogen compounds, sulfur compounds, aliphatic oxygenated compounds, halogenated compounds, organophosphate compounds, phosphonothionate compounds, phosphorothionate compounds, arsenic compounds, chloroethyl compounds, phosgene, cyanic compounds, and a combination thereof.

31. The method of claim 26, wherein the contaminant is selected from the group consisting of: acetaldehyde, methyl mercaptan, ammonia, hydrogen sulfide, diethyl sulfide, diethyl disulfide, dimethyl sulfide, dimethyl disulfide, trimethylamine, styrene, propionic acid, n-butyric acid, n-valeric acid, iso-valeric acid, pyridine, formaldehyde, 2-chloroethyl ethyl sulfide, carbon monoxide, and a combination thereof.

* * * * *

UNITED STATES PATENT AND TRADEMARK OFFICE
CERTIFICATE OF CORRECTION

PATENT NO.         : 7,655,594 B2                                    Page 1 of 1
APPLICATION NO. : 10/512336
DATED              : February 2, 2010
INVENTOR(S)        : Okun et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1463 days.

Signed and Sealed this

Twenty-third Day of November, 2010

David J. Kappos
*Director of the United States Patent and Trademark Office*